United States Patent [19]

Ackermann et al.

[11] 4,377,532

[45] Mar. 22, 1983

[54] 3-PHENOXYBENZYL COMPOUNDS

[75] Inventors: Peter Ackermann, Reinach; Laurenz Gsell, Basel; Rudolf Wehrli, Rheinfelden, all of Switzerland

[73] Assignee: Ciba-Geigy Corporation, Ardsley, N.Y.

[21] Appl. No.: 350,453

[22] Filed: Feb. 19, 1982

[30] Foreign Application Priority Data

Feb. 26, 1981 [CH] Switzerland .................. 1296/81
Nov. 9, 1981 [CH] Switzerland .................. 7169/81

[51] Int. Cl.³ .................. C07C 121/80; C07C 121/75; C07C 43/295; C07C 47/575
[52] U.S. Cl. .................. 260/465 E; 260/465 F; 260/465 D; 564/74; 564/430; 568/441; 568/638
[58] Field of Search .................. 260/465 E, 465 F; 564/74, 430; 568/441, 638

[56] References Cited

U.S. PATENT DOCUMENTS 4,024,163 5/1977 Elliott et al. .................. 260/347.4
4,058,622 11/1977 Fujimoto et al. .................. 424/308

*Primary Examiner*—Dolph H. Torrence
*Attorney, Agent, or Firm*—Frederick H. Rabin

[57] ABSTRACT

The invention relates to 3-phenoxybenzyl compounds of the formula

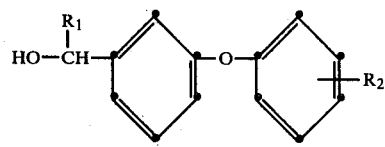

wherein $R_1$ is hydrogen, cyano, —CSNH$_2$, C$_2$–C$_3$alkenyl or C$_2$–C$_3$alkynyl and $R_2$ is alkenyl or alkynyl, as intermediates for the production of biocides.

The preparation of the 3-phenoxybenzaldehydes employed as intermediates is described. Novel 3-phenoxybenzaldehydes used as starting materials and the production thereof are also disclosed.

10 Claims, No Drawings

3-PHENOXYBENZYL COMPOUNDS

The present invention relates to 3-phenoxybenzyl compounds, to the production thereof and to the use thereof as intermediates for the synthesis of biocides.

The 3-phenoxybenzyl compounds of the invention have the formula

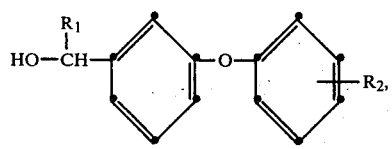

wherein $R_1$ is hydrogen, cyano, $-CSNH_2$, allenyl, $C_2-C_3$ alkenyl or $C_2-C_3$ alkynyl, and $R_2$ is alkenyl or alkynyl.

Alkenyl or alkynyl groups suitable for $R_2$ may be straight chain or branched, unsubstituted or substituted, and the double or triple bond is conjugated with the phenyl nucleus. Alkenyl and alkynyl groups $R_2$ contain preferably 2 to 6, especially 2 to 3, carbon atoms.

Examples of preferred substituents carried by these groups are: cyano, halogen such as fluorine, chlorine, bromine or iodine, with bromine or iodine being preferred, and $C_1-C_6$ alkyl, $C_1-C_6$ hydroxyalkyl, $C_1-C_6$ haloalkyl or dimethylamino.

Interesting intermediates are compounds of formula I, wherein $R_1$ is hydrogen, cyano, allenyl or ethynyl, and $R_2$ is p-vinyl, p-1-propenyl, p-3-dimethylamino-1-propenyl, p-ethynyl, p-1-propynyl, p-iodoethynyl or p-3-dimethylamino-1-propynyl.

Particularly interesting intermediates, however, are compounds of formula I, wherein $R_1$ is hydrogen or cyano, and $R_2$ is p-vinyl, p-1-propenyl, p-ethynyl or p-1-propynyl.

The compounds of formula I can be obtained by methods which are known per se, e.g. as follows:

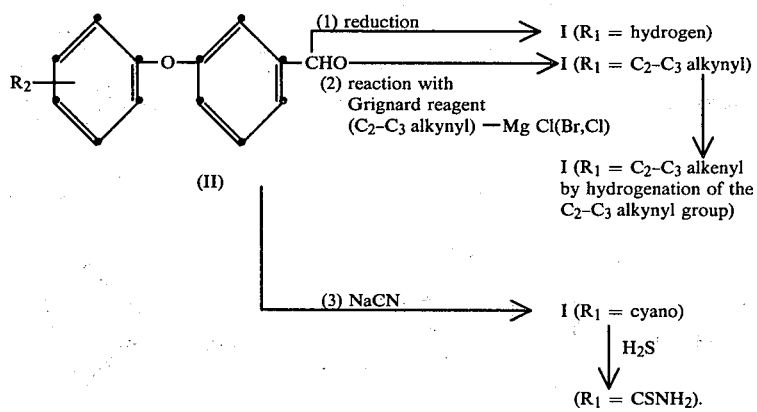

$R_2$ in formula II is as defined for formula I.

The processes are carried out at a reaction temperature in the range from $-10°$ to $100°$ C., with the preferred range being from $0°$ to $80°$ C., in general under normal pressure and, if desired, in an inert solvent or diluent. Suitable solvents or diluents are, in particular, ethers such as diethyl ether, tetrahydrofurane or dioxane for the second process, whereas it is preferred to use an alcohol such as methanol or ethanol for processes 1 and 3.

The compounds of formula II, which can be obtained by methods which are known per se, are novel and likewise constitute an object of the present invention.

The compounds of formula I are suitable for use as intermediates for the production of e.g. pyrethroids (cf. Example 2), which are suitable for controlling insects of the family Arthropoda, such as of the classes insecta and Arachnoida.

EXAMPLE 1: Preparation of m-(p-ethynylphenoxy)benzyl alcohols

Reaction scheme:

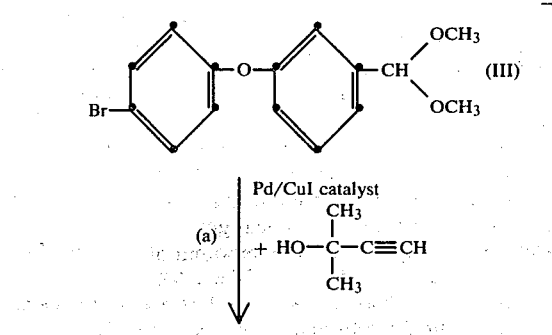

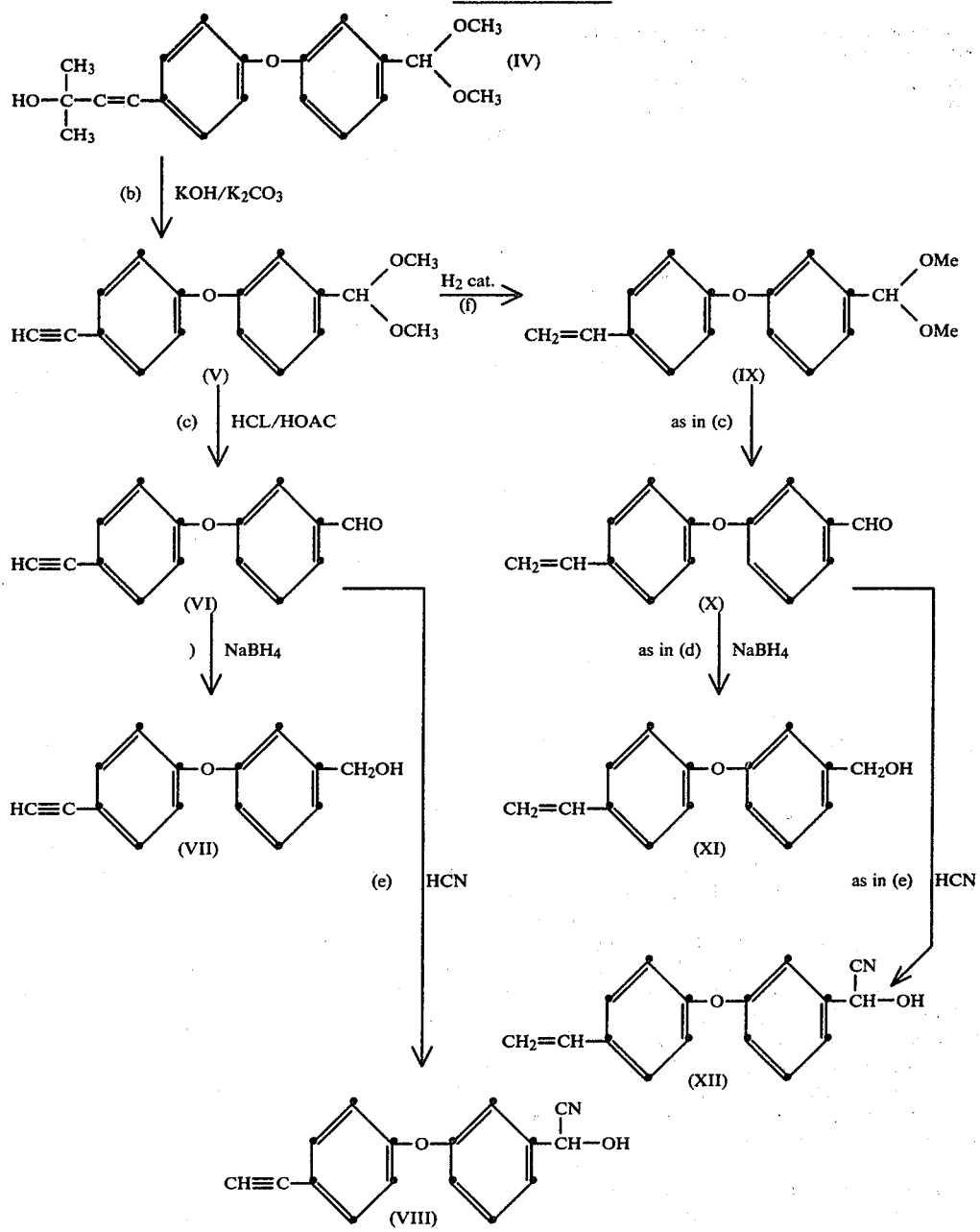

(a) A mixture of 33.5 g of the compound of formula III, 13.1 g of 2-methyl-3-butin-2-ol, 104 ml of triethylamine, 0.73 g of (Ph$_3$P)$_2$ PdCl$_2$ and 0.4 g of CuI is heated to 80° C. The mixture is stirred for 16 hours at 80° C., filtered, and the filtrate is extracted with ether. The ethereal phase is washed with ammonium chloride and then with sodium chloride solution, dried over magnesium sulfate and concentrated.

The crude product is chromatographed over silica gel with ether/hexane (1:1) as eluant, to give the compound of the formula IV with a refractive index of $n_D^{20°} = 1.5445$.

(b) A mixture of 50 g of the compound of formula IV, 5 g of KOH and 50 g of K$_2$CO$_3$ in 500 ml of toluene is heated to 140° C. The toluene is distilled off and the residue is chromatographed over silica gel with hexane/ether (10:1) as eluant, to give the compound of the formula V with a refractive index of $n_D^{20°} = 1.5748$.

(c) 17.9 g of the compound of formula V, 67 ml of 2 N HCl and 33.5 ml of glacial acetic acid are stirred for 2 hours at 60° C. The reaction mixture is poured into sodium acetate and extracted with ethyl acetate. The ethyl acetate phase is washed twice with sodium acetate and once with saturated sodium chloride solution, dried over magnesium sulfate and dried. The crude product is chromatographed over silica gel with hexane/ether (5:1) as eluant, to give the compound of the formula VI with a refractive index of $n_D^{20°} = 1.6009$.

(d) 0.18 g of NaBH$_4$ and 1.4 ml of water are put into a reactor under nitrogen. With cooling, 3.5 g of the aldehyde of formula VI in 11.4 ml of methanol are slowly added dropwise. The reaction mixture is stirred for 12 hours at 20° C., then diluted with water and extracted twice with CH₂Cl. The organic phase is washed with saturated sodium chloride solution and dried over magnesium sulfate. The crude product is chromatographed over silica gel with hexane/ether (1:1) as eluant, affording the compound of the formula VII with a refractive index of $n_D^{20°} = 1.5942$.

(e) To 3.3 g of sodium cyanide in 4 ml of water and 87 ml of methanol are added dropwise, at 0° C., first 10 g of the aldehyde of the formula VI

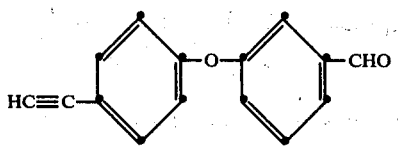

in 10 ml of methanol and then 10.3 ml of acetic acid. The reaction mixture is stirred for 2 hours at 20° C., then poured into iced water and extracted with CH₂Cl. The organic phase is extracted once with sodium acetate and twice with iced water, dried over magnesium sulfate, filtered and concentrated, affording the desired α-cyanobenzyl alchol (formula VIII) with a refractive index of $n_D^{20°} = 1.6049$.

(f) Hydrogen is introduced at 20° C. into a solution of 10 g of the compound of formula V in 100 ml of dimethyl formamide with 1 g of Lindlar catalyst. After the uptake of 1 equivalent of hydrogen, the reaction mixture is filtered and the solvent is removed under reduced pressure, affording the compound of the formula XI with a refractive index of $n_D^{20°} = 1.5828$.

The compound of the formula X with a refractive index of $n_D^{30°} = 1.6128$ is obtained from the compound of formula IX by a procedure similar to that of step (c). The compound of the formula XI with a refractive index of $n_D^{30°} = 1.6061$ is obtained from the aldehyde of formula X in a manner similar to that of step (e). The compound of the formula XII with a refractive index of $n_D^{30°} = 1.5963$ is obtained from the compound of formula XI in a manner similar to that of step (e).

The following compounds are also prepared in similar manner and by known methods.

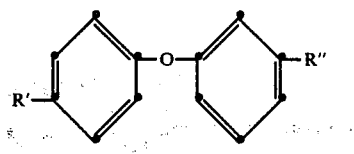

| R' | R'' | Physical data |
|---|---|---|
| $CH_3-C\equiv C-$ | $-CH\begin{smallmatrix}OCH_3\\OCH_3\end{smallmatrix}$ | $n_D^{20°} = 1.5911$ |
| $CH_3-C\equiv C-$ | $-CHO$ | $n_D^{30°} = 1.6212$ |
| $CH_3-C\equiv C-$ | $\begin{smallmatrix}CN\\\|\\-CH-OH\end{smallmatrix}$ | $n_D^{20°} = 1.6071$ |

-continued

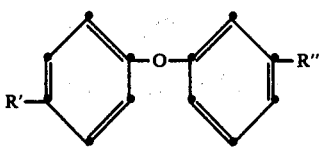

| R' | R'' | Physical data |
|---|---|---|
| $CH_3-C\equiv C-$ | $\begin{smallmatrix}C\equiv OH\\\|\\-CH-OH\end{smallmatrix}$ | $n_D^{20°} = 1.6159$ |
| $CH_3-C\equiv C-$ | $\begin{smallmatrix}CH=C=CH_2\\\|\\-CH-OH\end{smallmatrix}$ | $n_D^{20°} = 1.6128$ |
| $CH_3-CH=CH-$ | $-CH_2OH$ | $n_D^{20°} = 1.6057$ |
| $CH_3-CH=CH-$ | $-CH\begin{smallmatrix}OCH_3\\OCH_3\end{smallmatrix}$ | $n_D^{20°} = 1.5790$ |
| $CH_3-CH=CH-$ | $-CHO$ | $n_D^{20°} = 1.640$ |
| $CH_3-CH=CH-$ | $\begin{smallmatrix}CN\\\|\\-CH-OH\end{smallmatrix}$ | $n_D^{20°} = 1.6094$ |
| $I-C\equiv C-$ | $-CH\begin{smallmatrix}OCH_3\\OCH_3\end{smallmatrix}$ | m.p.: 72–74° C. |
| $I-C\equiv C-$ | $-CHO$ | m.p.: 106–111° C. |
| $I-C\equiv C-$ | $\begin{smallmatrix}CN\\\|\\-CH-OH\end{smallmatrix}$ | $n_D^{20°} = 1.6013$ |
| $(CH_3)_2N-CH_2-CH=CH-$ | $-CHO$ | $n_D^{20°} = 1.5922$ |
| $(CH_3)_2N-CH_2-CH=CH-$ | $\begin{smallmatrix}CN\\\|\\-CH-OH\end{smallmatrix}$ | $n_D^{20°} = 1.5687$ |
| $(CH_3)_2N-CH_2-C\equiv C-$ | $-CHO$ | $n_D^{20°} = 1.6018$ |
| $(CH_3)_2N-CH_2-C\equiv C-$ | $\begin{smallmatrix}CN\\\|\\-CH-OH\end{smallmatrix}$ | $n_D^{20°} = 1.6220$ |

EXAMPLE 2: Preparation of the biocide of the formula

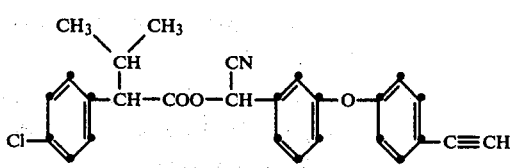

(XIII)

To a solution of 2.3 g of the compound of the formula

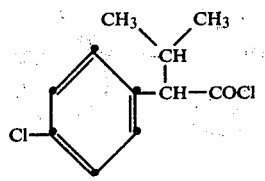

in 20 ml of toluene are added dropwise, at 0° C., first 1 ml of pyridine and then a solution of 5.4 g of the compound of the formula

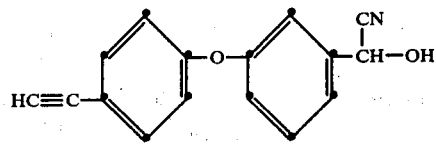

in 20 ml of toluene.

The reaction mixture is stirred for 12 hours at 20° C., then poured into 2 N hydrochloric acid, extracted once with 10% potassium carbonate solution, once with saturated sodium carbonate solution and once with saturated sodium chloride solution. The extracts are dried over magnesium sulfate, filtered and concentrated. The crude product is chromatographed over silica gel with toluene as eluant, affording the compound of the formula XIII with a refractive index of $n_D^{20°} = 1.5811$.

What is claimed is:

1. A 3-phenoxybenzyl alcohol of the formula

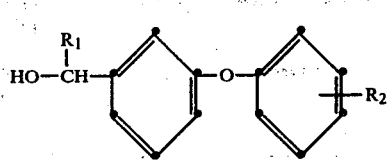

wherein $R_1$ is hydrogen, cyano, —CSNH$_2$, allenyl, $C_2$–$C_3$ alkenyl or $C_2$–$C_3$ alkynyl, and $R_2$ is alkenyl or alkynyl.

2. A compound according to claim 1, wherein $R_1$ is hydrogen, cyano, allenyl or ethynyl, and $R_2$ is p-vinyl, p-1-propenyl, p-3-dimethylamino-1-propenyl, p-ethynyl, p-1-propynyl, p-iodoethynyl or p-3-dimethylamino-1-propynyl.

3. A compound according to claim 2, wherein $R_1$ is hydrogen or cyano, $R_2$ is p-vinyl, p-1-propenyl, p-ethynyl or p-1-propynyl, and $X_1$ is hydroxyl.

4. The compound according to claim 3 of the formula

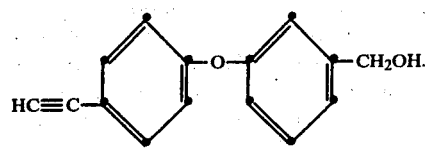

5. The compound according to claim 3 of the formula

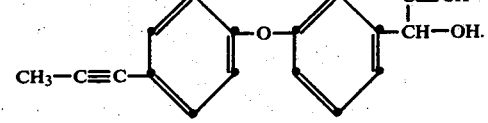

6. The compound according to claim 3 of the formula

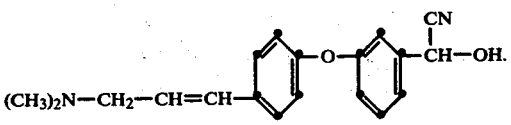

7. The compound according to claim 2 of the formula

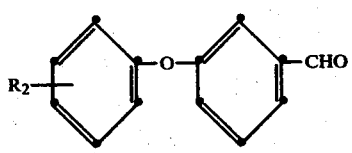

8. The compound according to claim 2 of the formula

9. The compound according to claim 2 of the formula

10. A 3-phenoxybenzaldehyde of the formula wherein $R_2$ is as defined in claim 1.

* * * * *